(12) United States Patent
Akbar et al.

(10) Patent No.: US 7,303,723 B2
(45) Date of Patent: Dec. 4, 2007

(54) METHOD OF FORMING NANOSTRUCTURES ON CERAMICS

(75) Inventors: Sheikh A. Akbar, Hilliard, OH (US); Sehoon Yoo, Columbus, OH (US); Kenneth H. Sandhage, Atlanta, GA (US)

(73) Assignee: The Ohio State University Research Foundation, Columbus, OH (US)

( * ) Notice: Subject to any disclaimer, the term of this patent is extended or adjusted under 35 U.S.C. 154(b) by 569 days.

(21) Appl. No.: 10/678,772

(22) Filed: Oct. 3, 2003

(65) Prior Publication Data

US 2004/0126624 A1 Jul. 1, 2004

Related U.S. Application Data

(60) Provisional application No. 60/416,124, filed on Oct. 4, 2002.

(51) Int. Cl.
*C04B 41/00* (2006.01)
(52) U.S. Cl. .................. 264/677; 977/763
(58) Field of Classification Search ......... 264/646, 264/340, 666, 677; 977/762, 763, 840
See application file for complete search history.

(56) References Cited

U.S. PATENT DOCUMENTS

| | | | | |
|---|---|---|---|---|
| 4,900,698 A * | 2/1990 | Lundsager | ............... | 501/80 |
| 5,177,034 A * | 1/1993 | Jean et al. | ............... | 501/17 |
| 5,205,991 A * | 4/1993 | Avery et al. | ............... | 422/129 |
| 5,406,058 A * | 4/1995 | Lipp | ............... | 219/774 |
| 5,538,681 A * | 7/1996 | Wu | ............... | 264/432 |
| 5,763,344 A * | 6/1998 | Komatsu | ............... | 501/98.4 |
| 5,814,262 A * | 9/1998 | Ketcham et al. | ............... | 264/316 |
| 6,159,831 A | 12/2000 | Thrush et al. | | |
| 6,231,744 B1 | 5/2001 | Ying et al. | | |
| 6,270,571 B1 | 8/2001 | Iwasaki et al. | | |
| 6,313,015 B1 | 11/2001 | Lee et al. | | |
| 6,359,288 B1 | 3/2002 | Ying et al. | | |
| 6,596,078 B2 * | 7/2003 | Konakahara et al. | ............... | 117/75 |
| 6,596,187 B2 * | 7/2003 | Coll et al. | ............... | 216/56 |

(Continued)

FOREIGN PATENT DOCUMENTS

CN 1358670 7/2002

(Continued)

OTHER PUBLICATIONS

M. P. Harold, et al.; Catalysis with inorganic membranes; MRS Bulletin, 1994. 19(4): p. 34-9.

(Continued)

*Primary Examiner*—Carlos Lopez
(74) *Attorney, Agent, or Firm*—Jason H. Foster; Kremblas, Foster, Phillips & Pollick

(57) ABSTRACT

A method for manufacturing oriented arrays of ceramic or metal oxide nanostructures, such as titania ($TiO_2$) nanofibers. The nanofibers are formed on the surface of a body that is first sintered at a temperature in the range of about 1,100 to about 1,400 degrees Celsius. Subsequently, the surface is exposed to an $H_2$-bearing gas, such as $H_2$ and $N_2$ in a ratio of about 5:95 at about 700 degrees Celsius for about 8 hours. During heat treatment in the gas phase reaction, sintered titania grains transform into arrays of nanofibers oriented in the same crystallographic direction.

29 Claims, 13 Drawing Sheets

U.S. PATENT DOCUMENTS

| | | | |
|---|---|---|---|
| 2001/0000889 | A1 | 5/2001 | Yadav et al. |
| 2002/0001977 | A1 | 1/2002 | Gole et al. |
| 2003/0126742 | A1 | 7/2003 | Ting et al. |

FOREIGN PATENT DOCUMENTS

| | | |
|---|---|---|
| CN | 1419846 | 5/2003 |
| DE | 10064865 | 7/2002 |
| JP | 2000-203998 A2 | 7/2000 |
| JP | 2000203998 | 7/2000 |
| JP | 2002-34531 A2 | 2/2002 |
| JP | 2002034531 | 2/2002 |
| JP | 2002-67000 A2 | 3/2002 |
| JP | 2002067000 | 3/2002 |
| JP | 2002-154819 A2 | 5/2002 |
| JP | 2002154819 | 5/2002 |
| JP | 2003-71799 A2 | 3/2003 |
| JP | 2003071799 | 3/2003 |
| JP | 2003-191200 A2 | 7/2003 |
| JP | 2003191200 | 7/2003 |
| TW | 444067 | 7/2001 |
| WO | WO 98/48456 | 10/1998 |
| WO | WO 03/053851 | 7/2003 |

OTHER PUBLICATIONS

Xagas, Androulaki, Hiskia, & Falaras; Preparation, fractal surface morphology and photocatalytic properties of TiO2 films. Thin Solid Films, 1999. 357(2): p. 173-178.

O.K.Varghese, et al.; Crystallization and high-temperature structural stability of titanium oxide nanotube arrays. Journal of Materials Research, 2003. 18(1): p. 156-165.

O'Regan & Graetzel; A low cost, high-efficiency solar cell based on dye-sensitized colloidal titanium dioxide films. Nature (London, United Kingdom), 1991. 353(6346): p. 5017-18.

Marguerettaz & Fitzmaurice; Heterosupramolecular chemistry: long-lived charge trapping by vectorial electron flow in a heterotriad. Journal of the American Chemical Society, 1994 116(11): p. 5017-18).

Kasuga, etal.; Formation of Titanium Oxide Nanotube. Langmuir, 1998. 14(12): p. 3160-3163.

Kasuga, etal.; Titania nanotubes prepared by chemical processing. Advanced Materials (Weinheim, Germany), 1999. 11(15): p. 1307-1311.

Gong, etal.; Titanium oxide nanotube arrays prepared by anodic oxidation. Journal of Materials Research, 2001. 16(12): p. 3331-3334.

Michailowski, Almawlawi, Cheng & Moskovits; Highly regular anatase nanotuble arrays fabricated in porous anodic templates. Chemical Physics Letters, 2001. 349 (1,2): p. 1-5.

Imai, etal.; Direct preparation of anatase TiO2 nanotubes in porous alumina membranes. Journal of Materials Chemistry, 1999. 9(12): p. 2971-2972.

Du, etal.; Preparation and structure analysis of titanium oxide nanotubes. Applied Physics Letters, 2001, 79(22): p. 3702-3704.

Sugiura, Yoshida & Minoura; Designing a TiO2 nano-honeycomb structure using photoelectrochemical etching. Electrochemical and Solid-State Letters, 1998. 1(4): p. 175-177.

Imhof & Pine; Ordered Macroporous materials by emulsion templating. Nature(London), 1997. 389(6654): p. 948-951.

Barin; Thermochemical Data of Pure Substances. ed., ed. vol. 48, 573, 620, 622, 700, 702, 703, 1213, 1690-1696, 1775, 1778-1780. 1995, Weinheim, Germany: VCH Verlagsgesellschaft.

Lynch & Bullard; Phase equilibria in the titanium-oxygen system. Metallurgical and Materials Transactions B: Process Metallurgy and Materials Processing Science, 1997, 28B(3): p. 447-453.

Catlow; Defect clustering in nonstoichiometric oxides, in Nonstoichiom. Oxides, O. Sorensen, EditorEditors. 1981, Academic Press, Inc.: New York. p. 61-98.

* cited by examiner

METHOD OF FORMING NANOSTRUCTURES ON CERAMICS

CROSS-REFERENCES TO RELATED APPLICATIONS

This application claims the benefit of U.S. Provisional Application No. 60/416,124 filed Oct. 4, 2002.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

This invention relates generally to methods for heat-treating ceramics, and more particularly to a novel method for heat treating ceramics to form nanostructures, such as nanofibers, on the surfaces thereof.

2. Description of the Related Art

It is well known that various ceramics can be used as catalysts and gas sensors. Titanium oxide ($TiO_2$), or titania, has shown significant promise in the gas sensor field. Titania can be used as a sensor by placing a titania structure, such as a fiber or a disk, in an electrically conductive path and exposing the structure to a gas. If the gas contains, for example, hydrogen, hydrogen ions permeate the surface of the structure. These hydrogen ions provide electrons for conductivity, thereby altering the structure's resistance to the flow of electrical current. The change in the electrical resistance of the structure can be measured, and related to the concentration of hydrogen in the gas.

Generally, gas sensors and catalysts require high exposed surface area to allow for efficient reactions with the gas. Too little exposed surface area produces too small of a change in resistivity of the sensor in a given time, thereby making rapid measurement of slight changes in gas composition difficult. Thus, any sensing or catalyzing structure must have high surface area for gas-to-solid interaction that can be measured effectively, and rapidly.

Increasing surface area without making the sensing structure larger has been the focus of a significant amount of research. This has resulted in the conventional understanding that high surface area structures can be achieved by the formation of nanowires, nanotubes and nanopores on the surface of the sensing structure.

For titania, one of the important engineering materials, the nanostructured surfaces possess an extensive range of applications, e.g. photocatalysts and supports, chemical sensors, photovoltaic solar cells, and photoelectrochromic devices, and biomedical devices. Various fabrication methods such as anodization, electrodeposition, and photoelectrochemical etching have been used to obtain titania surfaces having a nanowires, nanotube and nanopore form. Most of these fabrication methods, however, are complicated and expensive due to the use of templates or the multiple chemical processes involved in the methods. Furthermore, some of these methods require post-annealing to transform as-fabricated, amorphous $TiO_2$ into crystalline form.

There is therefore a need for a less complex and inexpensive method for forming high surface area structures on the surface of titania and other ceramics.

BRIEF SUMMARY OF THE INVENTION

The present invention is an easier and less expensive method for manufacturing oriented arrays of ceramic nanostructures. A nanostructure is a structure, including but not limited to fibers, particles and films, having at least one dimension (e.g., thickness, diameter, width, etc.) that is less than one micron, preferably less than 100 nanometers, and most preferably less than or equal to 50 nanometers. In a preferred embodiment of the invention, titania ($TiO_2$) nanofibers are formed having diameters between about 15 and about 50 nm. These nanofibers are formed on the surface of a structure that is exposed to a reducing environment, preferably $H_2$-bearing gases at modest temperatures. During heat treatment in the gas containing hydrogen, sintered titania grains transform into arrays of nanofibers oriented in the same crystallographic direction.

More specifically, the invention is a method of forming ceramic nanofibers on the surface of a solid body, and the invention includes the solid body with the fibers formed. The preferred method comprises a first step of compressing titania particulate at a pressure greater than about 0 MPa, and preferably about 400 MPa, to form a solid body. The preferred second step is sintering the solid body in air at a temperature of between about 1,100 and about 1,400 degrees Centigrade, preferably about 1,200 degrees Centigrade, for about 6 hours. The preferred third step, which preferably follows the first and second steps, is heat-treating the solid body in a gas mixture that contains an inert gas and a hydrogen containing gas, such as $H_2$, and preferably a majority inert gas and minority hydrogen-containing gas. In a preferred embodiment, the gas mixture is at about 700 degrees Celsius, the gas mixture contains about 95 percent inert gas, such as $N_2$, and about 5 percent hydrogen-containing gas, such as $H_2$, and the gas flow rate is between about 100 and about 500 milliliters per minute. Preferably the flow rate is at least about 500 milliliters.

The method described above is a surprisingly simple and highly-scalable method that has been discovered for "carving" oriented arrays of single crystal titania nanofibers from bulk titania crystals via reaction with a hydrogen-bearing gas. The bulk crystals undergoing this reaction can be present on the external surfaces of dense, polycrystalline titanium oxide pellets. The structures containing these oriented arrays of single crystal titania nanofibers can be used as reactive or catalytic surfaces for gas sensors, fuel cells and catalysts applications, among others that will be recognized by the person having ordinary skill in the art from the present description.

The nanofibers formed by the preferred embodiment are about 15-50 nm in diameter and up to about 5 μm in length, which corresponds to an aspect ratio of about 50:1 to about 100:1. This provides high surface area for gas-solid interaction, which is beneficial for chemical sensors and catalysts. The process described demonstrates the feasibility of a simple, low-cost method of fabricating nano-structured ceramics. Other potential applications include, but are not limited to, photocatalytic and antimicrobial-related devices. Moreover, this technique may provide a new avenue for micro-machining of ceramics, which is often a non-trivial task.

BRIEF DESCRIPTION OF THE SEVERAL VIEWS OF THE DRAWINGS

FIGS. 2C and 2D show nanofibers formed on the disks' surfaces after exposure to a flowing gas mixture of $H_2$ and $N_2$.

Figure 1:
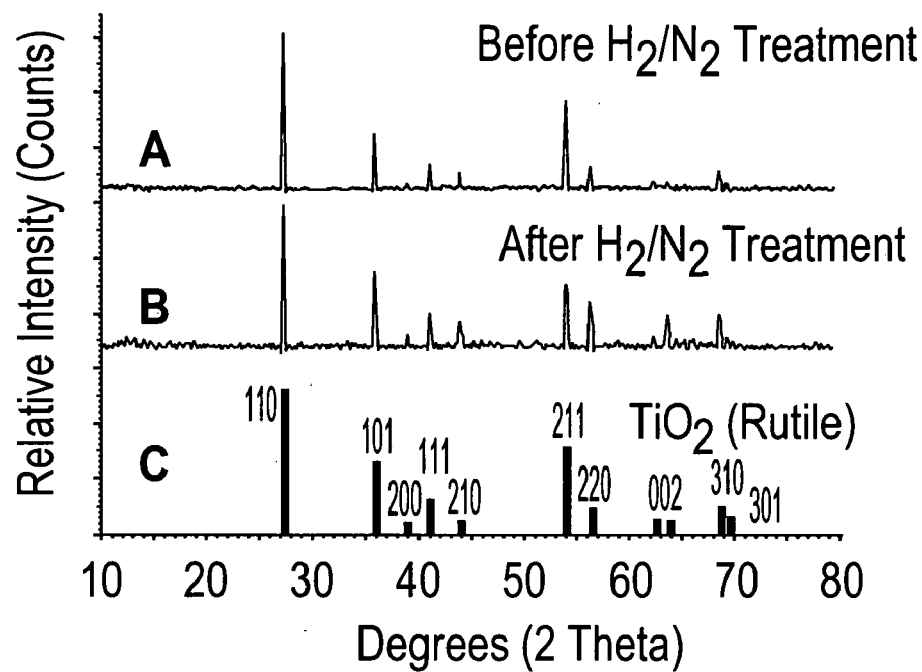
FIG. 1 is an x-ray diffraction analysis of sintered titania specimens.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or terms similar thereto are often used. They are not limited to direct connection, but include connection through other elements where such connection is recognized as being equivalent by those skilled in the art.

DETAILED DESCRIPTION OF THE INVENTION

Several experiments were performed in accordance with the present invention. The experiments began with commercial anatase $TiO_2$ powder that is 99.9% pure, and can be obtained from Alfa Aesar, Ward Hill, Mass. The powder possessed an average particle size of 32 nm, and was compacted with a uniaxial press into disk-type green compacts at a peak stress of about 392 MPa.

The "green" compacts were sintered for 6 hours in the range of 1,100° C. to 1,400° C. in air. The sintered samples possessed bulk densities of 4035±85 kg/m$^3$, which corresponds to 94.9±2.0% of the theoretical density of rutile (4250 kg/m$^3$). After this sintering treatment, the disks were about 1.0 mm thick and about 10 mm in diameter.

The surfaces of the disks were next converted into titania nanofiber arrays by exposing the disks to a flowing gas mixture containing about 5% $H_2$ and about 95% $N_2$ at 700° Centigrade for up to about 8 hours within a horizontal tube furnace. The flow rate of the gas mixture was set at a rate between about 100 and about 500 milliliters per minute. The oxygen partial pressure within the furnace was about $10^{-19}$ Pa.

Once the experiments were concluded, the disks were examined using various devices to determine the surface structures. A field emission gun scanning electron microscope was used to characterize the surface morphology of the titania specimens before and after the $H_2/N_2$ gas treatment. Additionally, x-ray diffraction analyses were used to evaluate the phase content of the disk surfaces before and after the $H_2/N_2$ gas treatment. Furthermore, the structure and chemistry of the titanium oxide nanofibers were examined with transmission electron microscopy. Still further, the nanofibers were removed from the specimen surfaces by exposure to ultrasonic energy during immersion in methanol. The nanofibers were then collected onto a carbon-coated copper grid for TEM analyses (bright field imaging, selected area electron diffraction analyses, and energy dispersive x-ray analyses). The results of these examinations are shown in the figures, and are discussed in more detail below.

X-ray diffraction analysis of the sintered titania specimens revealed peaks for only the rutile polymorph of titanium oxide, shown in FIG. 1. These X-ray diffraction patterns that were obtained are shown in FIG. 1 as A, which is the specimen before the gas treatment and B, which is the specimen after exposure to the 5% $H_2$/95% $N_2$ mixture for 8 hours at 700° C. Diffraction peaks in A and B are consistent with those in C for the rutile polymorph of $TiO_2$, which is shown as C.

Figure 2A:
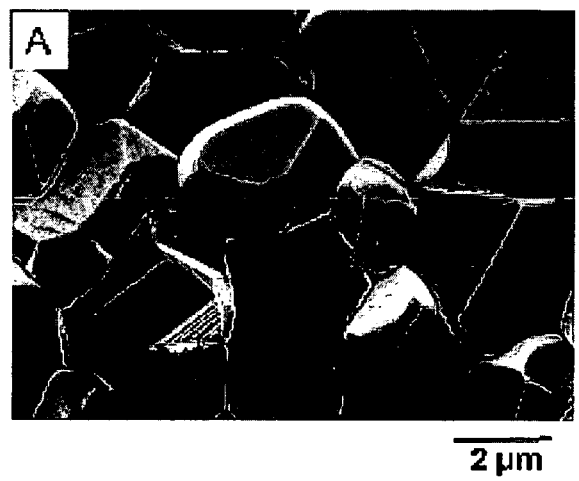
FIGS. 2A, 2B, 2C and 2D are scanning electron micrographs of the surfaces of titania disks after sintering heat treatment.
Figure 2B:
Figure 2C:
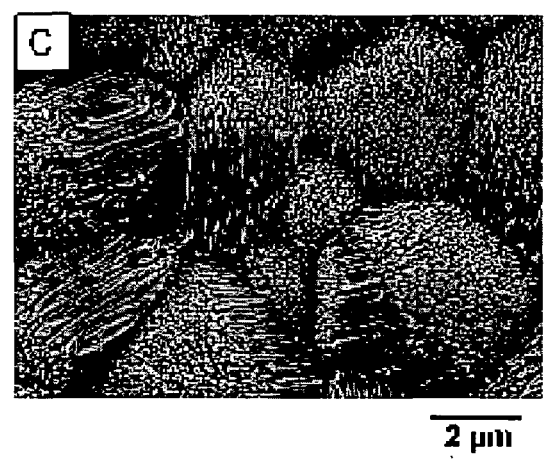
Figure 2D:
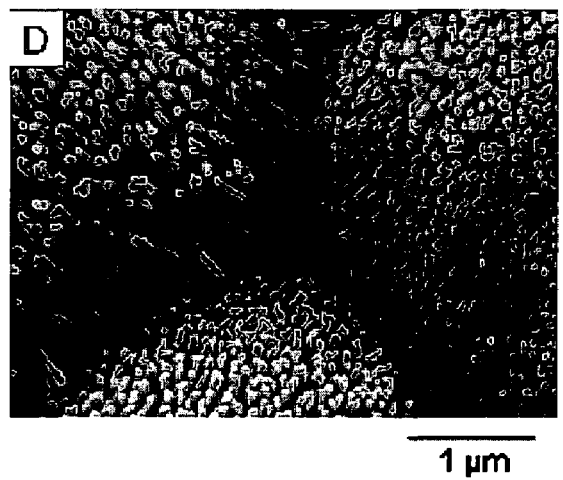

Scanning electron micrographs of the surface of the titania disks after the sintering heat treatment at 1,200° C. for 6 hours in air are shown in FIGS. 2A and 2B, which show the rutile grains on the disk surface. As described above, the dense rutile disks were subsequently exposed to a flowing 5% $H_2$/95% $N_2$ gas mixture at 700° C. for 8 hours. FIGS. 2C and 2D show the nanofibers formed on the disk surface after exposure to the flowing gas mixture. The average size of the rutile grains was 4.0 μm.

These scanning electron micrographs show the dramatic morphological change resulting from the $H_2/N_2$ treatment. Fine fibers, with diameters of about 15-50 m and lengths of up to 5 μm, are observed to have formed on the external specimen surface. Such nanofibers were organized into aligned arrays. The sizes of these aligned fiber arrays were similar to the sizes of the rutile grains observed in the starting specimens, which can be seen when FIG. 2A is compared to FIG. 2C. As described in relation to FIG. 1, x-ray diffraction patterns obtained from the nanofiber-bearing surfaces shown in FIGS. 2C and 2D revealed diffraction peaks for only rutile.

In order to determine whether the titania nanofibers were formed by outward growth from the starting rutile surface (e.g., by evaporation and redeposition in an epitaxial manner onto the underlying rutile grains) or by the inward growth of nanochannels (e.g., by selective gas-phase etching of the rutile along preferred crystallographic directions), secondary electron images were obtained from the same rutile grains before and after exposure to the 5% $H_2$/95% $N_2$ gas mixture for various time periods. These images are shown in FIGS. 3A, 3B and 3C.

Figure 3A:
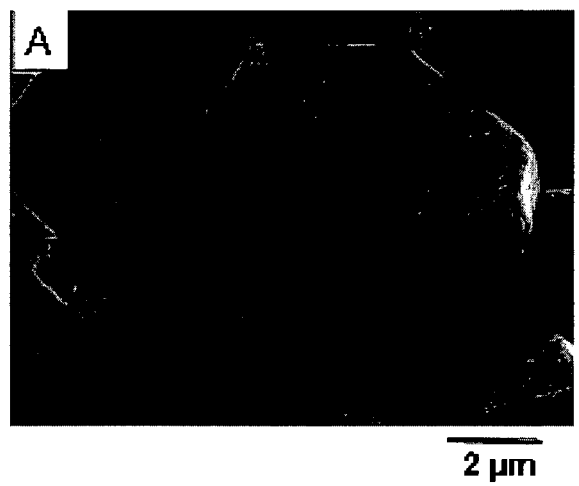
FIG. 3A is a scanning electron micrograph of titania grains on a sintered specimen before exposure to the $H_2/N_2$ gas mixture.

FIG. 3A shows the grains before exposure to the $H_2/N_2$ gas mixture. Within 10 minutes of exposure to the gas mixture, fine channels formed on certain surfaces of the rutile grains as shown in FIG. 3B. Nanoparticles can also be seen on some surfaces of the rutile grains. After prolonged exposure up to 8 hours, the channels had increased in depth and had become interconnected so that discrete, aligned nanofibers were generated from a given rutile grain as shown in FIG. 3C. Arrays of oriented nanofibers were generated from the dense rutile grains seen in FIG. 3A. The overall size and shape of each aligned nanofiber array were similar to those of the starting rutile grain from which the array was derived. These observations clearly indicate that the formation of the aligned nanofiber arrays was the result of an etching process and not a deposition process. The etching process was also selective with respect to the crystallography of rutile.

Figure 4A:
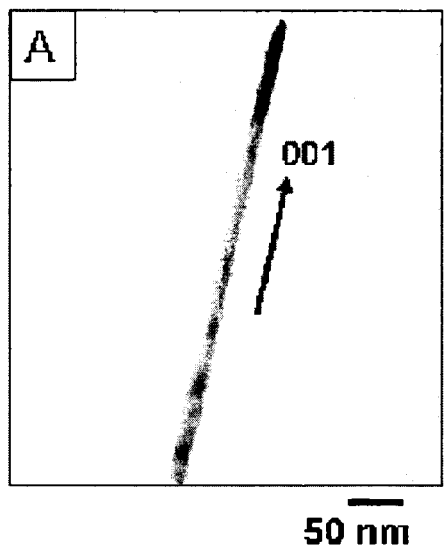
FIG. 4A is a bright field TEM image of a titania nanofiber.
Figure 4B:
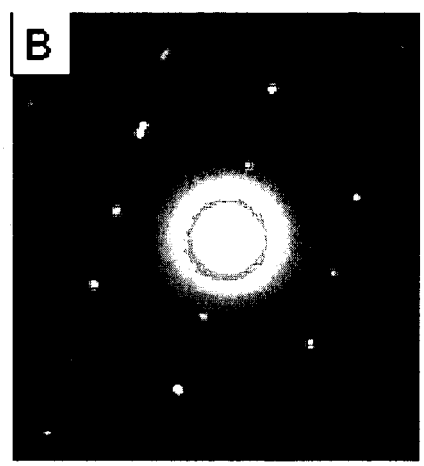
FIG. 4B is an associated selective area electron diffraction pattern of a titania nanofiber.

Nanofibers that were formed during exposure to the $H_2/N_2$ gas mixture were ultrasonically removed from specimen surfaces and examined by transmission electron microscopy (TEM). A bright field TEM image of a nanofiber, and an associated selective area electron diffraction (SAED) pattern, are shown in FIGS. 4A and 4B, respectively. The SAED patterns obtained at various positions along the length of a given nanofiber indicated that each nanofiber was comprised of a single rutile crystal. The rings observed in the SAED pattern in FIG. 4B were generated by the carbon-coated grid used to support the specimen during TEM analysis. The SAED analysis also revealed that the long dimension, i.e., the fiber axis, of each nanofiber was parallel to the [001] crystallographic direction of rutile.

Figure 3B:
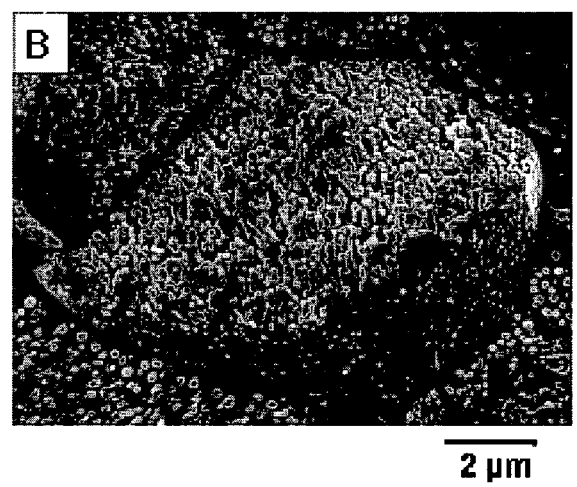
FIG. 3B is a scanning electron micrograph of titania grains on a sintered specimen after 10 minutes of exposure to the $H_2/N_2$ gas mixture.
Figure 3C:
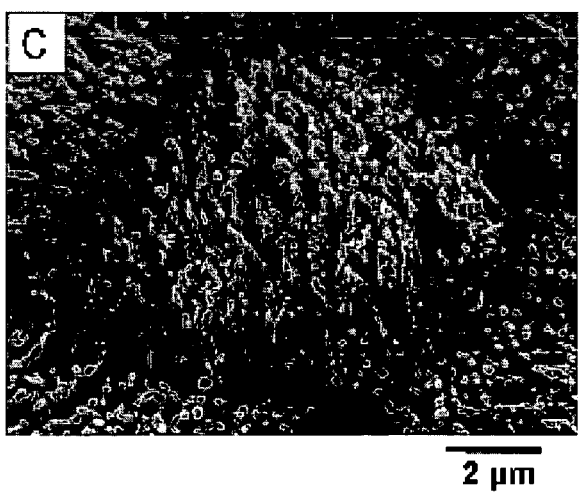
FIG. 3C is a scanning electron micrograph of titania grains on a sintered specimen after exposure to the $H_2/N_2$ gas mixture of up to 8 hours.
Figure 4C:
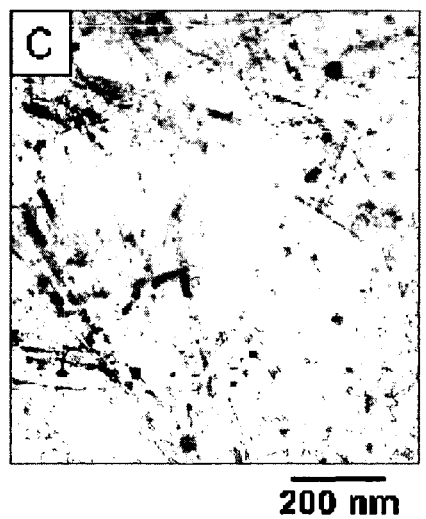
FIG. 4C is a bright field TEM image of titania nanofibers and nanoparticles.
Figure 4D:
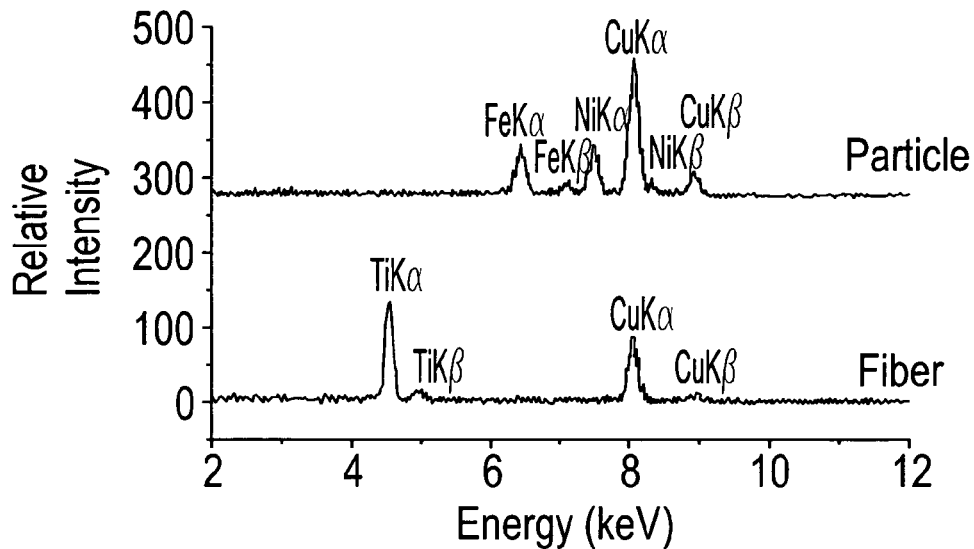
FIG. 4D is the result of an energy dispersive x-ray analysis of a titania nanoparticle and a titania nanofiber.

SEM analysis of specimens exposed to the $H_2/N_2$ gas treatment also revealed the presence of small, spherical nanoparticles on the external specimen surfaces, as can be seen in FIGS. 3B and 3C. A bright field TEM image of the nanofibers and nanoparticles is shown in FIG. 4C. The result of an energy dispersive x-ray (EDX) analysis of a nanoparticle and a nanofiber is shown in FIG. 4D. EDX analysis indicated that these nanoparticles were enriched in iron and nickel, relative to the titania-based nanofibers. It is theorized that the nanoparticles were generated during the $H_2/N_2$ gas treatment by the external reduction of the iron and nickel oxides present as impurities in the starting titania powder. Inductively-coupled plasma (ICP) analysis indicated that the titania powder contained 0.027 wt % nickel and 0.015 wt % iron in the form of oxide impurities. Other impurities included copper (0.068 wt %), aluminum (0.041 wt %), chromium (0.018 wt %), and vanadium (0.010 wt %). The copper peaks in FIG. 4D were generated by the carbon-coated copper grid used to support the sample. Although copper is also likely to have been present in the nanoparticles, unambiguous detection of copper in these particles by EDX analysis was complicated by the signal generated by the carbon-coated copper grid used to support the specimens during TEM analyses. The absence of aluminum, chromium, and vanadium in the nanoparticles is likely to be due to the enhanced thermodynamic stabilities of the oxides of these elements relative to the oxides of nickel, iron, and copper.

The oxygen partial pressure established by the flowing 5% $H_2$/95% $N_2$ gas mixture at 700° C. was measured with an oxygen sensor to be $10^{-19}$ Pa. The phase stability diagram reported for the Ti—O system indicates that a slightly reduced form of titanium oxide, $TiO_{2-x}$ with x=0.02, should be stable under these conditions. Such a $TiO_{2-x}$ stoichiometry could, in principle, be achieved by the generation of point defects, such as titanium interstitials or oxygen vacancies, or by extended defects, such as shear planes or stacking faults, such as are present in the so-called Magneli phases. Extended defects were not observed in the nanofibers by high-resolution TEM analysis, which suggests that the nanofibers are comprised of slightly-reduced rutile containing primarily point defects.

Figure 5:
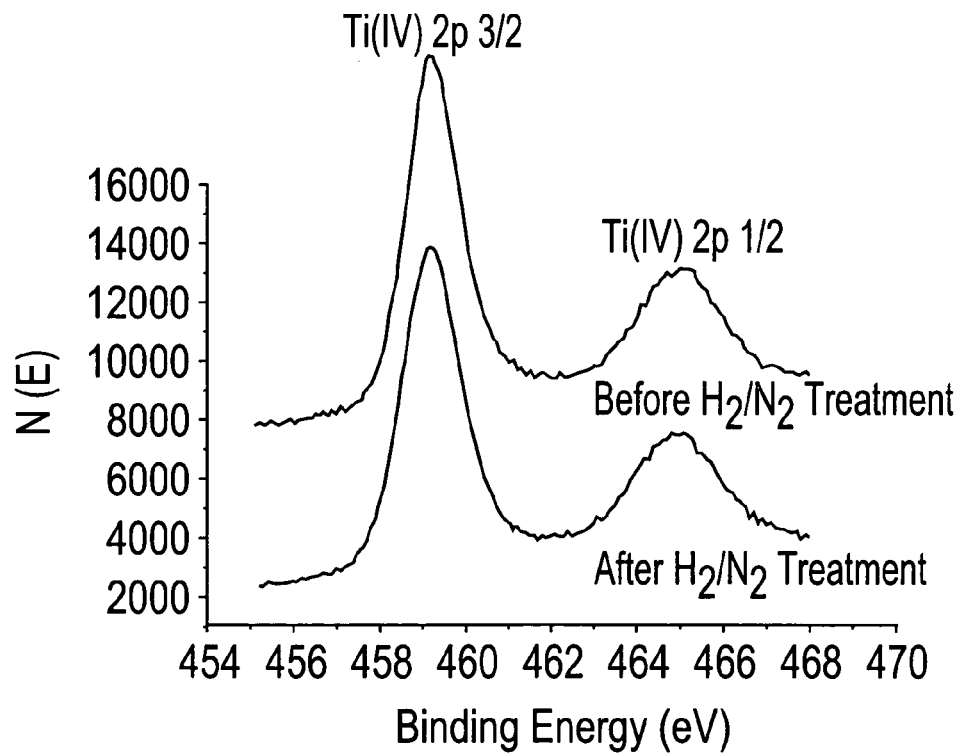
FIG. 5 is the result of x-ray photoelectron spectroscopy of titania specimens before and after an $H_2/N_2$ treatment.

The results of x-ray photoelectron spectroscopy (XPS) of specimens before and after the $H_2/N_2$ treatment is shown in FIG. 5. The binding energy of the peaks represented Ti (IV) 2p and the peak was not changed after $H_2/N_2$ treatment. Therefore, the inventors concluded that most of the titanium atoms were in the state of 4+ after the $H_2/N_2$ treatment.

Figure 11:
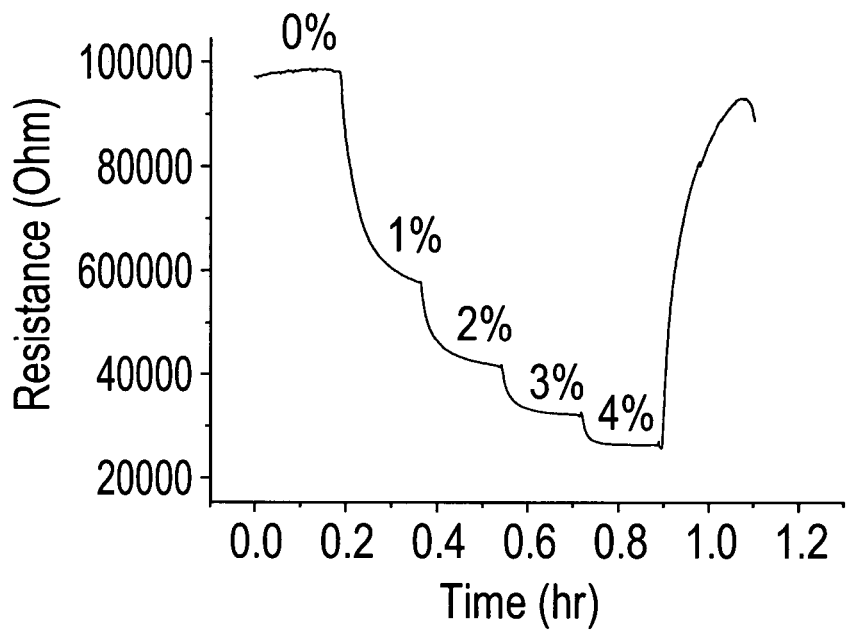
FIG. 11 is a graph of resistance versus time illustrating the electrical resistance of a titania sample exposed to varying percentages of hydrogen gas.

The fibers themselves were also tested for their performance in some of the contemplated uses of such fibers. A sensor device was fabricated using two strips of conductive gold paste, for providing electrical contact, painted on a surface. The sensor with nanofiber-covered surface was electrically connected to a resistance measuring device, and then exposed to a gas at 400° C. containing $H_2$ gas in the range of 0-4%. The sensing measurement was done inside a quartz tube, where the gas flow was controlled by mass flow controller. The electrical resistance of the titania sensors was measured using a digital multimeter and data were recorded by a computer. The results of these tests are shown in FIG. 11, which shows the dynamic response changes in electrical resistance of a sensor device exposed to the gas mixture containing the indicated amount of $H_2$ gas.

It will be understood by the person familiar with the technology that the parameters above, including temperature, time, gas composition, compression pressure, etc., can be varied to obtain variations in results. Although the formation of nanofibers requires the two-step heat treatment of sintering in air followed by exposure to a reducing environment, such as heat treatment in a hydrogen-containing gas, experimentation showed that there are a few important parameters to obtaining well-developed titania nanofibers, and some parameters that can be varied while still obtaining satisfactory results. These have not been explored fully, but some conclusions can be drawn.

First, before sintering, titania powder should be compressed with sufficient pressure. It will become apparent to the person of ordinary skill that more or less compaction pressure can be used than the 392 MPa that the inventors applied in their experiments, and this will produce different results than that obtained by the inventors. Different results may be desirable under some conditions. For the purposes of the present invention, the inventors contemplate a compaction pressure between about 0.0 MPa and about 400 MPa. Compaction at a pressure greater than about 400 MPa is within the scope of the invention, but is not considered necessary for the invention to produce satisfactory results.

Figure 6A:
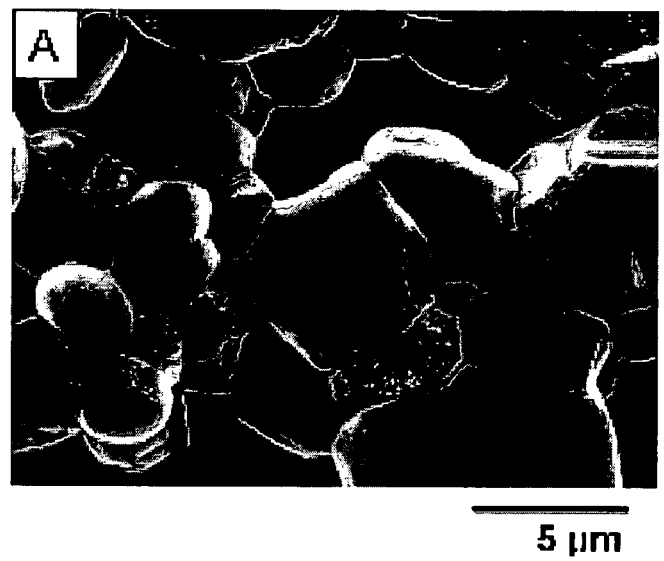
FIGS. 6A and 6B are scanning electron micrographs of a titania sample, shown in lower and higher magnification, respectively, that was compressed at about 0 MPa, then sintered at 1,200° C. and then heat treated in $H_2/N_2$ at 700° C.
Figure 6B:
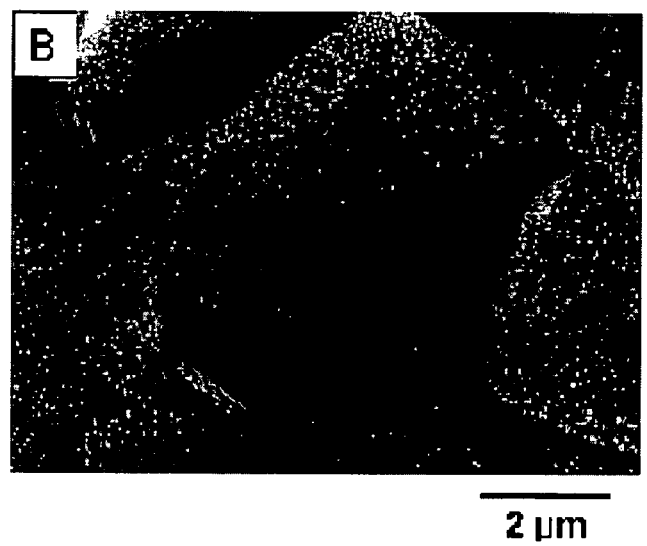

If the sample is sintered without powder pressing or the pressure of compaction is very low (near 0.0 MPa), the nanofibers may not form using the two-step heat treatment. The inventors normally compressed the powder with a pressure of about 400 MPa. However, when the load of the press was lowered to nearly 0.0 MPa and the two-step heat treatment was carried out, nanofibers were not observed on the surface, as shown in FIGS. 6A and 6B. The sample shown at low and high magnification in FIGS. 6A and 6B, respectively, was treated under the same conditions as the sample shown in FIG. 2, i.e., sintered at 1,200° C. and heat treated in $H_2/N_2$ at 700° C. No nanofiber formation is observed after $H_2/N_2$ treatment. In FIGS. 6A and 6B, the average grain size was estimated to be around 3.74 μm, which was slightly smaller than that of specimens pressed under 400 MPa. Compared with the titania surface compressed at about 400 MPa, the grain structure of the sample compressed at about 0 MPa was porous.

Figure 7A:
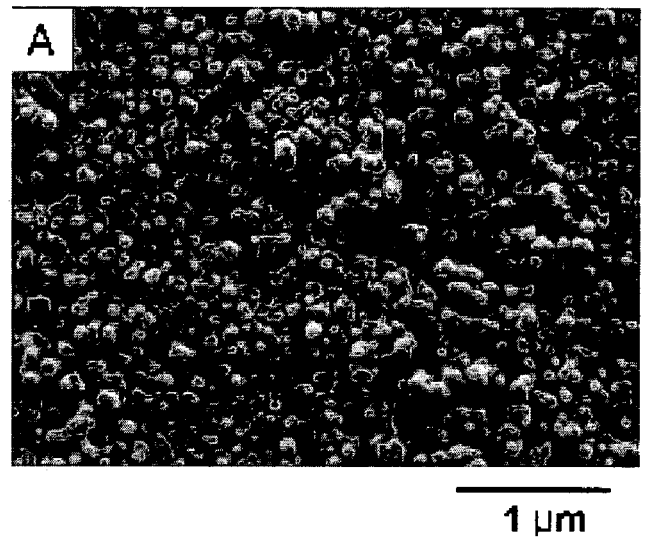
FIG. 7A is a scanning electron micrograph of a titania powder compact without sintering.
Figure 7B:
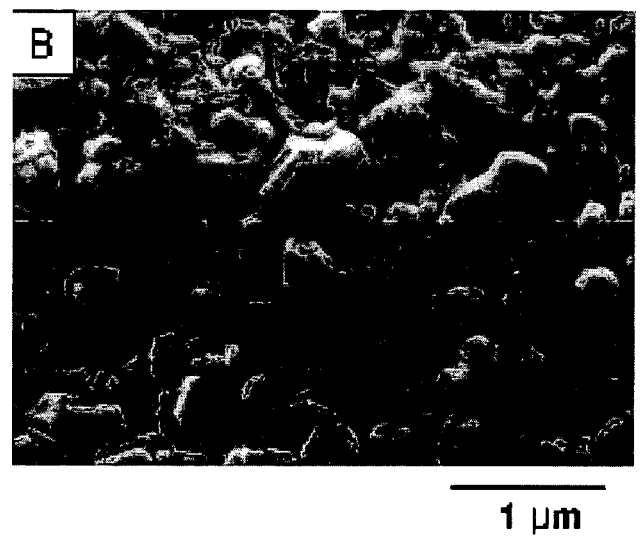
FIG. 7B is a scanning electron micrograph of the compact of FIG. 7A after $H_2/N_2$ treatment.

A second factor for achieving well-developed nanofibers is sintering. Without sintering, the nanofibers were not observed after $H_2/N_2$ treatment, as shown in FIG. 7A, which is a titania powder compact without sintering, and 7B, which is the compact that was not sintered after $H_2/N_2$ treatment. During the $H_2/N_2$ treatment grain growth occurred, as shown in FIG. 7B, but no fiber formation was observed.

It is known that sintering provides dense and large grain structures, but those grain structures are not the only condition for promoting nanofiber formation. The inventors tested titania single crystals, which are already dense, to see the results of the gas mixture treatment on them without sintering. When the titania single crystals were treated in $H_2/N_2$ with or without any prior sintering at 1,200° C., which is the same as the sintering temperature, the microstructure exhibited differences as shown in FIGS. 8A and 8B.

Figure 8A:
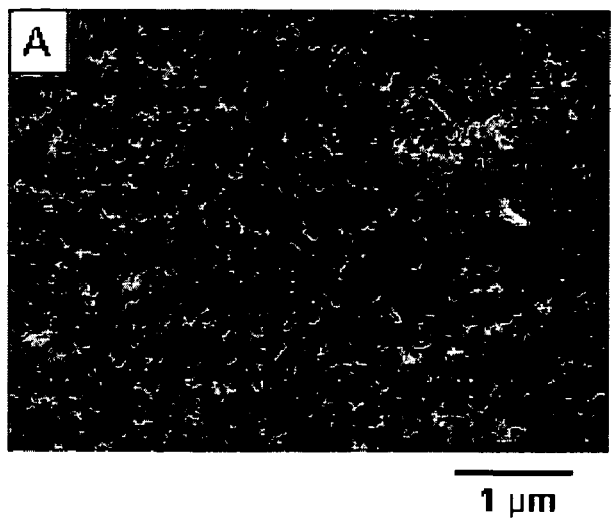
FIG. 8A is a scanning electron micrograph of a (001) titania single crystal without the heat treatment that is analogous to the preferred sintering step before the $H_2/N_2$ gas mixture treatment.

FIG. 8A shows a (001) titania single crystal without the prior sintering step before the $H_2/N_2$ gas mixture treatment. In FIG. 8A one can observe rectangularly shaped etch-pits. The etch-pits are formed along the direction perpendicular to the surface, which is the (001) direction. Also, the sides of the etch-pit rectangles are directed in the same direction. These arrangements of etch-pits indicate that the "nano-carving" process of the present invention depends on the crystallographic directions. It is apparent that the grooves leading to nanofibers form on {110} face but not on {100}. All nanofibers are aligned in the [001] direction. This confirms that the nanofibers are strongly dependent on the crystal orientation.

Figure 8B:
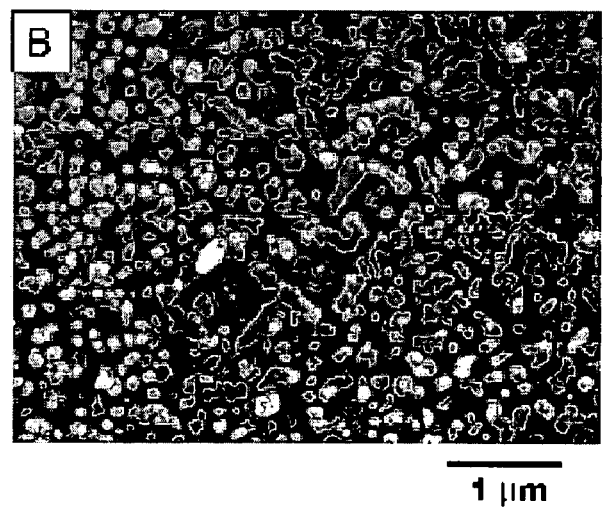
FIG. 8B is a scanning electron micrograph of a (001) titania single crystal which was heat treated at 1,200° C. for 6 hours and then treated in the $H_2/N_2$ gas mixture.
Figure 9A:
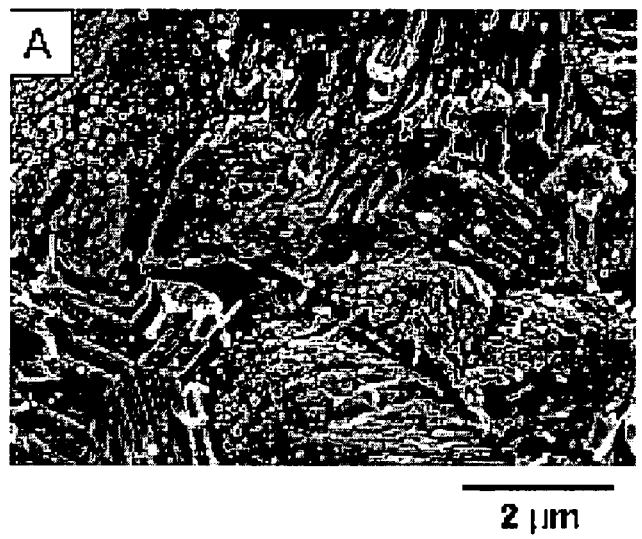
FIGS. 9A, 9B, 9C and 9D are scanning electron micrograph images of titania surfaces after heat-treatment of $H_2/N_2$ gas for samples sintered at different temperatures. The sintering temperatures were 1,100° C. for FIG. 9A, 1,200° C. for FIG. 9B, 1,300° C. for FIG. 9C and 1,400° C. for FIG. 9D.
Figure 9B:
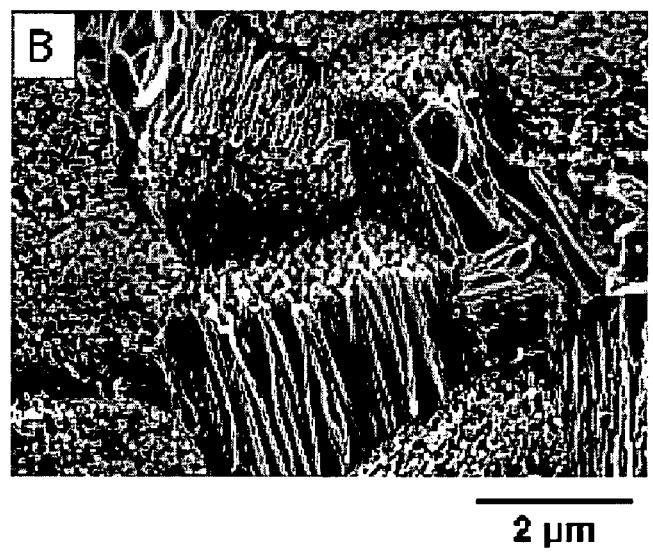
Figure 9C:
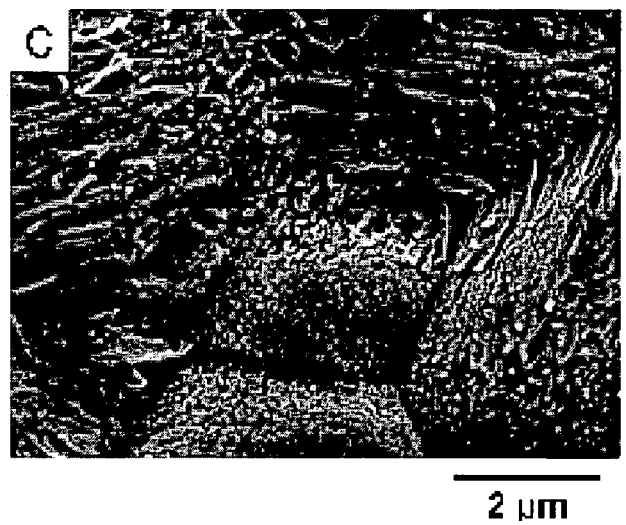
Figure 9D:
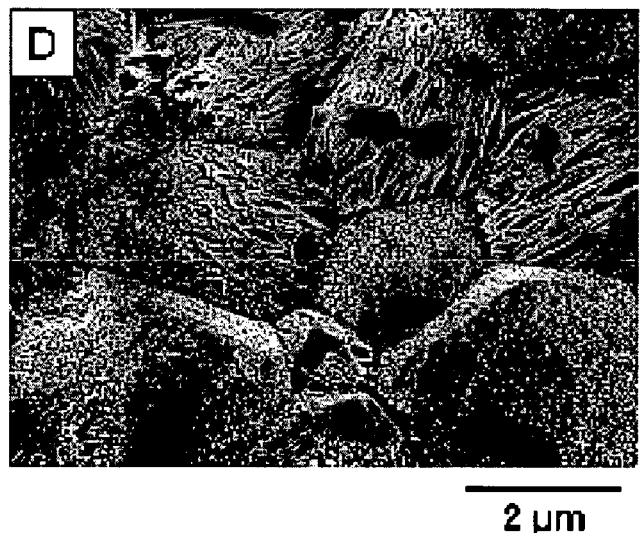

FIG. 8B shows a (001) titania single crystal which was sintered at 1,200° C. for 6 hours and then treated in the $H_2/N_2$ gas mixture. Unlike the specimen shown in FIG. 8A that did not have this "pre-heat-treatment", most of titania surface in FIG. 8B is etched, leaving short nanofibers. The result shows that more etching occurred for the pre-heat-treated single crystal than for the single crystal that was not sintered.

Nanofiber formation also depends on the sintering temperature. In order to understand the sintering temperature effect on the nanofiber formation, the sintering temperatures were varied in the range of 1,100-1,400° C. for 6 hours, and then the specimens were treated in the $H_2/N_2$ atmosphere at 700° C. for 8 hours. FIGS. 9A, 9B, 9C and 9D are SEM images of the titania surface after the reduction heat-treatment of $H_2/N_2$ gas for samples sintered at different temperatures. The sintering temperatures were 1,100° C. for FIG. 9A, 1,200° C. for FIG. 9B, 1,300° C. for FIG. 9C and 1,400° C. for FIG. 9D. For the lower two sintering temperatures, the fibers extended whole grains or grains were severely etched out. On the other hand, for the higher two sintering temperatures, the fibers formed only on the top faces of the grains. As sintering temperature increased, the formation of nanofibers became less pronounced. Therefore, as sintering temperature decreases, the nano-carving process becomes dominant.

Figure 10A:
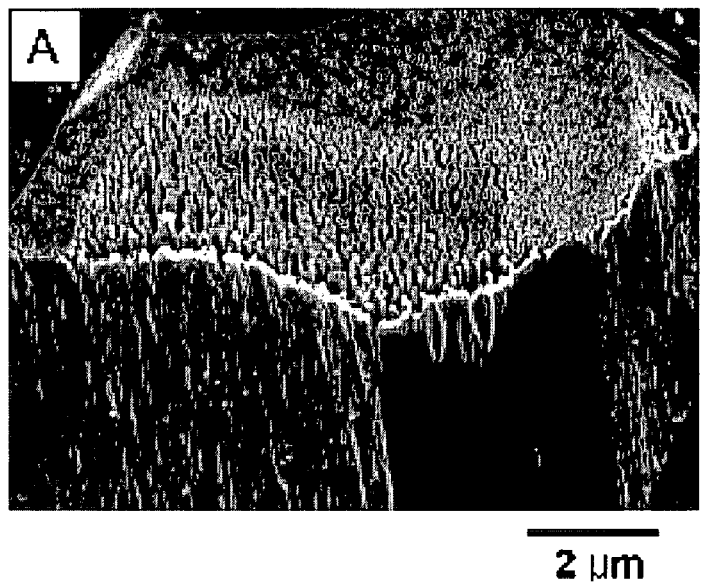
FIGS. 10A and 10B are scanning electron micrographs of titania heat-treated at 700° C. in the $H_2/N_2$ atmosphere at flow rates of 100 ml/min for FIG. 10A and 500 ml/min for FIG. 10B.
Figure 10B:
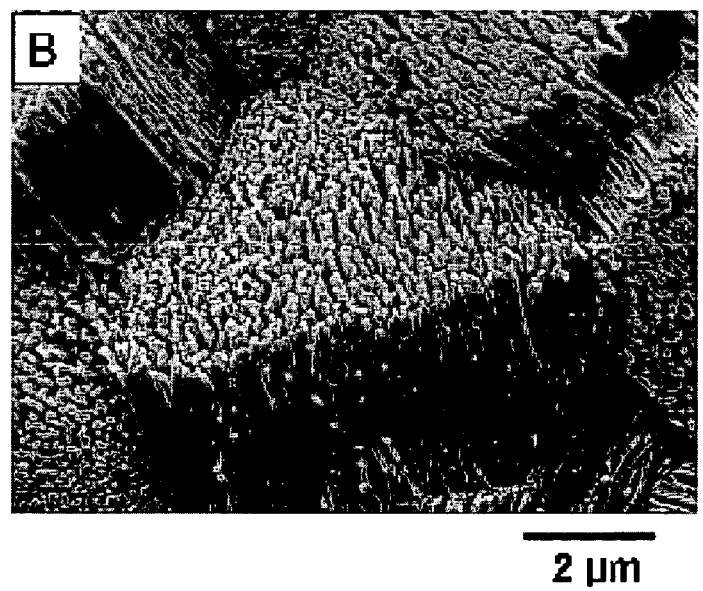

A third condition for well-developed nanofibers is the gas flow rate during the $H_2/N_2$ gas treatment. FIGS. 10A and 10B are scanning electron micrographs of titania heat-treated at 700° C. in the $H_2/N_2$ atmosphere. The flow rates were 100 ml/min for FIG. 10A and 500 ml/min for FIG. 10B. Nanofibers were formed in the whole grain at the higher flow rate, while nanofibers were only partially formed at the lower flow rate. Therefore, nanofiber formation depends on the gas flow rate, which suggests that nanofiber formation depends on evaporation of products or the diffusion of reactant gas through a gaseous boundary layer. Additionally, although nitrogen gas was used in the gas mixture of the preferred method, the inventors theorize that any inert gas can be used instead of nitrogen.

Because the preferred gas mixture of 95% $N_2$ and 5% $H_2$ produced satisfactory results, and because it can be inferred that other reducing environments, as well as other gases containing hydrogen, could produce satisfactory results, the inventors theorize that gas mixtures containing more or less hydrogen will also work. Although experiments heat treating the titania specimens with 100% $N_2$ did not produce nanofibers, it is theorized that gas mixtures with anywhere from a small minority (one to three percent) to a larger minority (more than 10 percent) of these gases would produce satisfactory results. It is also understood that any reducing environment could produce the same results.

Figure 13:
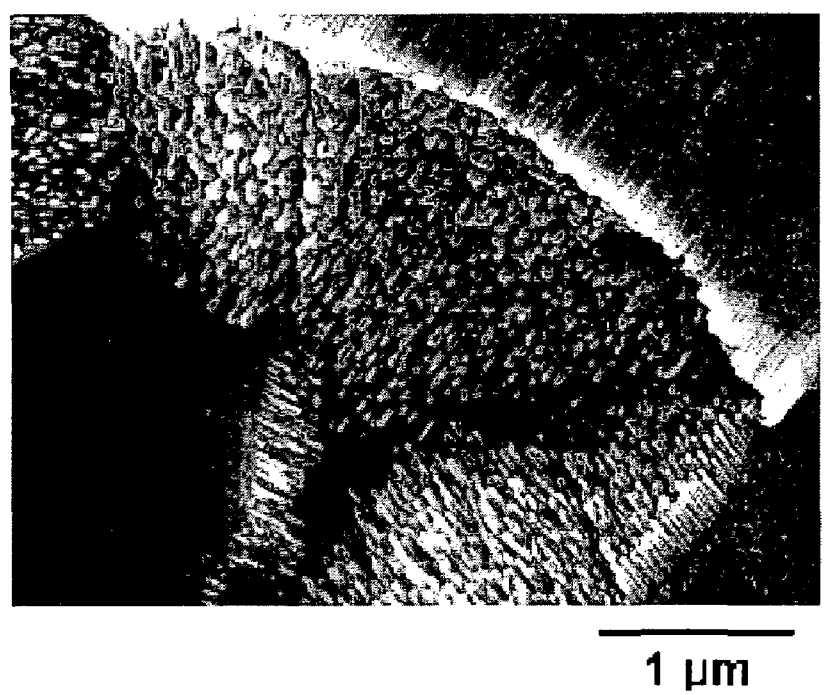
FIG. 13 is a scanning electron micrograph of a titania sample after heat-treatment in nitrogen carrying water vapor gas.

Nanofibers were also developed with heat-treatment at 700° C. in an atmosphere of $N_2$ gas with water vapor instead of $H_2$. FIG. 13 is a scanning electron micrograph of nanofibers formed after heat-treatment in $N_2$ carrying water vapor gas. The dimension of the nanofibers formed in water vapor atmosphere was much smaller than that of the nanofibers formed by $H_2/N_2$ treatment. For example, the diameter was around 10 nm in FIG. 13, which is about ⅕ the thickness of the nanofibers created by exposure to the $H_2/N_2$ gas mixture. Another distinctive feature of the nanofibers formed in water vapor atmosphere was that all nanofibers were formed only on a specific face (001) of the titania crystal. Moreover, the fibers appear to have been formed by deposition rather than etching, which is different than the case for $H_2/N_2$ atmosphere "nano-carving".

Figure 12:
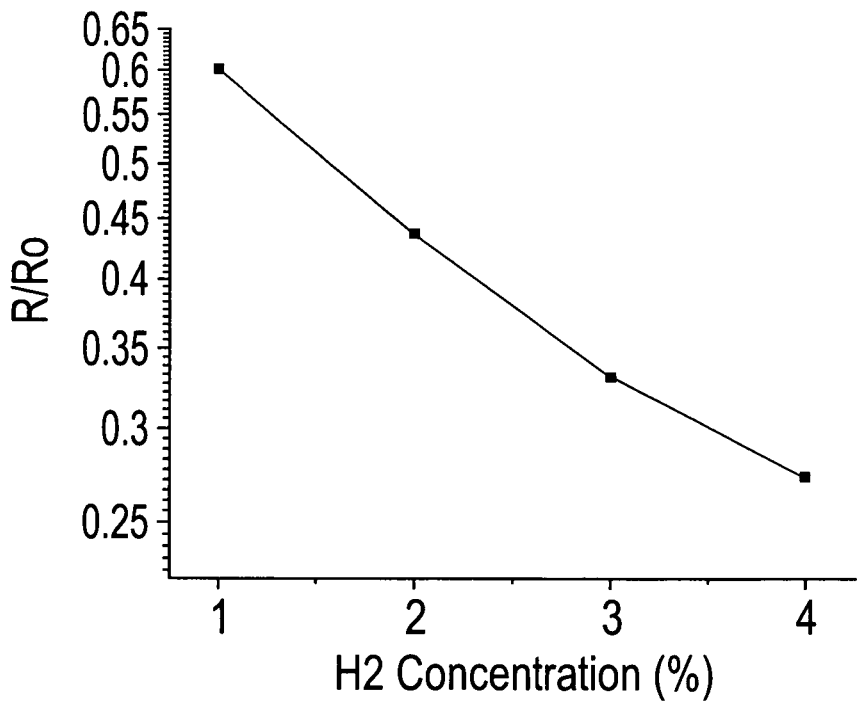
FIG. 12 is a graph of the sensitivity (R/Ro) of the nanofiber sensor versus concentration of hydrogen.

One of the potential applications of titania nanofibers is in the area of chemical sensors. As shown in FIG. 11, the electrical resistance of the $TiO_2$ sample changed rapidly when it was exposed to $H_2$ gas, and gradually became saturated. Comparing the results of the invention with sintered titania, which showed practically no response, the nanofiber-based sensor exhibits good response due to dramatically increased surface area. FIG. 12 shows the sensitivity (R/Ro) of the nanofiber sensor versus concentration of $H_2$. From FIG. 12, one can conclude that the nanofiber sensor shows relatively high sensitivity to hydrogen gas in particular, and reducing gases generally.

The inventors contemplate that the solid bodies with nanofibers on the surfaces, and the fibers themselves, will be useful as catalyst support, gas sensors, photoelectrochemical cells and in fuel cells. Other applications will become apparent to persons of ordinary skill in the art from the description herein.

While certain preferred embodiments of the present invention have been disclosed in detail, it is to be understood that various modifications may be adopted without departing from the spirit of the invention or scope of the following claims.

The invention claimed is:

1. A method of forming a ceramic body with nanostructures on at least one surface thereof, the method comprising:
    (a) compressing ceramic particulate at a pressure sufficient to form a solid body;
    (b) sintering the solid body at a temperature and for a period sufficient to bond the particulate in the solid body into one or more ceramic crystals; and
    (c) exposing the sintered solid body to a reducing environment at a temperature of about 700 degrees Celsius and for a period sufficient to form nanostructures on at least a portion of the exterior surface of the solid body.

2. The method in accordance with claim 1, wherein the ceramic particulate further comprises titania.

3. The method in accordance with claim 1, wherein the reducing environment further comprises a hydrogen-containing gas flowing over the solid body at a sufficient gas flow rate to form said nanostructures.

4. The method in accordance with claim 1, wherein said pressure is greater than about 0 MPa.

5. The method in accordance with claim 1, wherein said pressure is about 400 MPa.

6. The method in accordance with claim 1, wherein the step of sintering is carried out at a temperature of less than 1,400 degrees Celsius.

7. The method in accordance with claim 6, wherein the step of sintering is carried out at a temperature of about 1,200 degrees Celsius.

8. The method in accordance with claim 7, wherein the step of sintering is carried out for about 6 hours.

9. The method in accordance with claim 3, wherein the hydrogen-containing gas further comprises a majority inert gas and a minority hydrogen-containing gas.

10. The method in accordance with claim 9, wherein the hydrogen-containing as is hydrogen.

11. The method in accordance with claim 9, wherein the hydrogen-containing gas is water.

12. The method in accordance with claim 9, wherein the step of exposing is carried out for a period of about 8 hours.

13. The method in accordance with claim 3, wherein the step of exposing is carried out at a hydrogen-containing gas flow rate between about 100 and about 500 milliliters per minute.

14. The method in accordance with claim 13, wherein the flow rate is at least about 500 milliliters per minute.

15. The method in accordance with claim 1, wherein the nanostructures formed further comprise nanofibers.

16. A method of forming a metal oxide body with nanostructures on at least one surface thereof, the method comprising:
    (a) compressing metal oxide particulate at a pressure greater than 0 MPa to form a solid body;
    (b) sintering the solid body in air at a temperature of less than 1,400 degrees C.; and then
    (c) heat treating the sintered solid body in a gas mixture containing a majority of an inert gas and a minority of a hydrogen-containing gas at a temperature of about 700 degrees Celsius and at a gas flow rate and for a period sufficient to cause nanostructures to form on at least a portion of the exterior surface of the solid body.

17. The method in accordance with claim 16, wherein the nanostructures formed further comprise nanofibers.

18. The method in accordance with claim 16, wherein said pressure is about 400 MPa.

19. The method in accordance with claim 16, wherein the step of sintering is carried out at a temperature of about 1,200 degrees Celsius.

20. The method in accordance with claim 19, wherein the step of sintering is carried out for about 6 hours.

21. The method in accordance with claim 16, wherein the inert gas is nitrogen.

22. The method in accordance with claim 16, wherein the hydrogen-containing gas is hydrogen.

23. The method in accordance with claim 16, wherein the hydrogen-containing gas is water.

24. The method in accordance with claim 16, wherein said gas flow rate is between about 100 and about 500 milliliters per minute.

25. The method in accordance with claim 24, wherein the gas flow rate is at least about 500 milliliters per minute.

26. The method in accordance with claim 16, wherein the step of heat treating is caffied out for a period of about 8 hours.

27. A method of forming a titania body with nanofibers on at least one surface thereof, the method comprising:
    (a) compressing titania particulate at a pressure of about 400 MPa to form a solid body;
    (b) sintering the solid body in air at a temperature between about 1,100 and about 1,400 degrees Celsius for about 6 hours; and then
    (c) heat treating the sintered solid body in gas containing about 95 percent inert gas and about 5 percent hydrogen with a gas flow rate between about 100 and about 500 milliliters per minute and a gas temperature of about 700 degrees Celsius.

28. The method in accordance with claim 27, wherein the step of sintering is carried out at a temperature of about 1,200 degrees Celsius.

29. The method in accordance with claim 27, wherein the flow rate is at least about 500 milliliters per minute.

* * * * *

UNITED STATES PATENT AND TRADEMARK OFFICE
CERTIFICATE OF CORRECTION

PATENT NO. : 7,303,723 B2  Page 1 of 1
APPLICATION NO. : 10/678772
DATED : December 4, 2007
INVENTOR(S) : Sheikh A. Akbar et al.

It is certified that error appears in the above-identified patent and that said Letters Patent is hereby corrected as shown below:

Column 9, Claim 10 line 43, add --gas--, delete "as"

Column 10, Claim 16 (b) line 7, add --Celsius--, delete "C."

Signed and Sealed this

Eighth Day of April, 2008

JON W. DUDAS
*Director of the United States Patent and Trademark Office*